United States Patent
Serafica et al.

(10) Patent No.: US 7,704,523 B2
(45) Date of Patent: *Apr. 27, 2010

(54) MICROBIAL CELLULOSE WOUND DRESSING FOR TREATING CHRONIC WOUNDS

(75) Inventors: Gonzalo Serafica, Langhorne, PA (US); Richard Mormino, San Antonio, TX (US); Gerry Ann Oster, Langhorne, PA (US); Kevin E. Lentz, Perkasie, PA (US); Kevin P. Koehler, Delran, NJ (US)

(73) Assignee: Lohmann & Rauscher GmbH, Triesting (AT)

( * ) Notice: Subject to any disclaimer, the term of this patent is extended or adjusted under 35 U.S.C. 154(b) by 246 days.

This patent is subject to a terminal disclaimer.

(21) Appl. No.: 10/425,978

(22) Filed: Apr. 30, 2003

(65) Prior Publication Data

US 2004/0028722 A1    Feb. 12, 2004

Related U.S. Application Data

(63) Continuation-in-part of application No. 10/173,576, filed on Jun. 18, 2002, which is a continuation-in-part of application No. 10/132,171, filed on Apr. 26, 2002, now Pat. No. 7,390,499.

(51) Int. Cl.
| | |
|---|---|
| A61L 15/00 | (2006.01) |
| A61L 15/14 | (2006.01) |
| A61L 15/16 | (2006.01) |
| A61L 15/22 | (2006.01) |
| A61L 15/28 | (2006.01) |
| A61K 9/70 | (2006.01) |
| A61K 31/155 | (2006.01) |
| A61K 31/715 | (2006.01) |
| A61F 13/00 | (2006.01) |
| A61F 13/15 | (2006.01) |

(52) U.S. Cl. .................. 424/447; 424/443; 424/445; 424/446; 514/57; 514/635; 602/52

(58) Field of Classification Search .......... 424/443, 424/445, 446, 447; 602/43, 49, 52; 514/635, 514/57

See application file for complete search history.

(56) References Cited

U.S. PATENT DOCUMENTS

| | | | |
|---|---|---|---|
| 3,630,194 A | 12/1971 | Boardman | |
| 3,872,862 A | 3/1975 | Hume | |
| 4,588,400 A | 5/1986 | Ring et al. | |
| 4,643,181 A | 2/1987 | Brown | |
| 4,650,674 A | 3/1987 | Aggarwal et al. | |
| 4,655,756 A | 4/1987 | Fawkes | |
| 4,655,758 A | 4/1987 | Ring et al. | |
| 4,788,146 A | 11/1988 | Ring et al. | |
| 4,837,079 A | 6/1989 | Quantrille et al. | |
| 4,912,049 A | 3/1990 | Farah | |
| 4,942,128 A | 7/1990 | Brown, Jr. | |
| 5,749,842 A * | 5/1998 | Cheong et al. | 602/41 |
| 5,846,213 A | 12/1998 | Wan | |
| 5,942,218 A | 8/1999 | Kirschner et al. | |
| 6,008,254 A | 12/1999 | Kligman et al. | |
| 6,156,334 A | 12/2000 | Meyer-Ingold et al. | |
| 6,238,691 B1 | 5/2001 | Huang | |
| 6,320,093 B1 | 11/2001 | Augustine et al. | |
| 6,369,289 B1 | 4/2002 | Orr, III | |
| 6,706,279 B1 * | 3/2004 | Hazzi | 424/443 |
| 7,186,693 B2 | 3/2007 | Quirk | |
| 7,390,499 B2 | 6/2008 | Serafica et al. | |
| 2001/0041188 A1 * | 11/2001 | Gibbins et al. | 424/486 |
| 2002/0187167 A1 | 12/2002 | Vacher | |
| 2003/0088201 A1 * | 5/2003 | Darcey | 602/44 |
| 2003/0190339 A1 | 10/2003 | Skover | |
| 2003/0203013 A1 | 10/2003 | Serafica et al. | |
| 2004/0161453 A1 | 8/2004 | Serafica et al. | |
| 2005/0019380 A1 | 1/2005 | Hoon et al. | |

FOREIGN PATENT DOCUMENTS

DE    10022751    9/2001

OTHER PUBLICATIONS

Gerald S. Lazaarus, et al., "Definitions and Guidelines for Assessment of Wounds and Evaluation of Healing," *Arch. Dermatol.*, 1994, pp. 489-493; vol. 130.

Cosmetic and Drug Preservation: Principles and Practice, Ed. Jon I. Kabara, .Marcel Dekker, Inc., New York and Basel, 1994, pp. 728-730.

M. Schramm et al., "Factors affecting Production of Cellulose at the Air/Liquid Interface of a Culture of *Acetobacter sylinum*," *J. Gen. Microbiol.*, 1954, pp. 123-129, vol. 11.

J.D. Fontana, et al., *Acetobacter* Cellulose Pellicle as a Temporary Skin Substitute, *Applied Biochemistry and Biotechnology*, 1990, pp. 253-264, vol. 24/25.

(Continued)

*Primary Examiner*—Johann R Richter
*Assistant Examiner*—James H. Alstrum-Acevedo
(74) *Attorney, Agent, or Firm*—Stinson Morrison Hecker LLP

(57) ABSTRACT

The invention relates to a wound dressing comprising a microbial-derived cellulose for treatment of specific types of chronic wounds, including pressure sores, venous and diabetic ulcers. The wound dressing is capable of donating liquid to dry substances is also capable of absorbing exudating wounds.

19 Claims, 3 Drawing Sheets

OTHER PUBLICATIONS

Krystynowicz et al., "The evaluation of usefulness of microbial cellulose as a wound dressing material," Med. Fac. Landbouw. Univ. Gent, 65/3a, 2000, pp. 213-220.
Brown-Etris et al., "Evaluation of a Biosynthetic Material: A New Wound Dressing Concept," Abstract, 1 Sheet, presented as a poster around Apr. 1998.
"Some of These Companies Forecast Revenues of More Than $25 Million," May/Jun. 1999, 1 Sheet.
Redacted agreement, Exhibit A to Rule 132 Declaration of Russell Hoon.
Jun. 22, 1998 510(k) approval No. K974251 for X-Cell Wound Dressing (printed out from FDA web site).
Office Action filed in U.S. Patent 7,390,499 dated Jun. 13, 2007.
Amendment and Response filed in U.S. Patent 7,390,499 on Dec. 12, 2007.
Final Office Action filed in U.S. Appl. No. 10/173,576 dated Nov. 30, 2007.
Appeal Brief filed in U.S. Appl. No. 10/173,576 on Sep. 24, 2008.
Office Action filed in U.S. Appl. No. 10/732,802 dated Jun. 23, 2008.
Amendment and Response to Office Action filed in U.S. Appl. No. 10/732,802 on Nov. 24, 2008.
Office Action filed in U.S. Appl. No. 10/864,804 dated Jul. 22, 2008.
Amendment and Response to Office Action filed in U.S. Appl. No. 10/864,804 on Nov. 24, 2008.
Redacted agreement, Exhibit a to Rule 132 Declaration of Russell Hoon, Sep. 12, 2005.

* cited by examiner

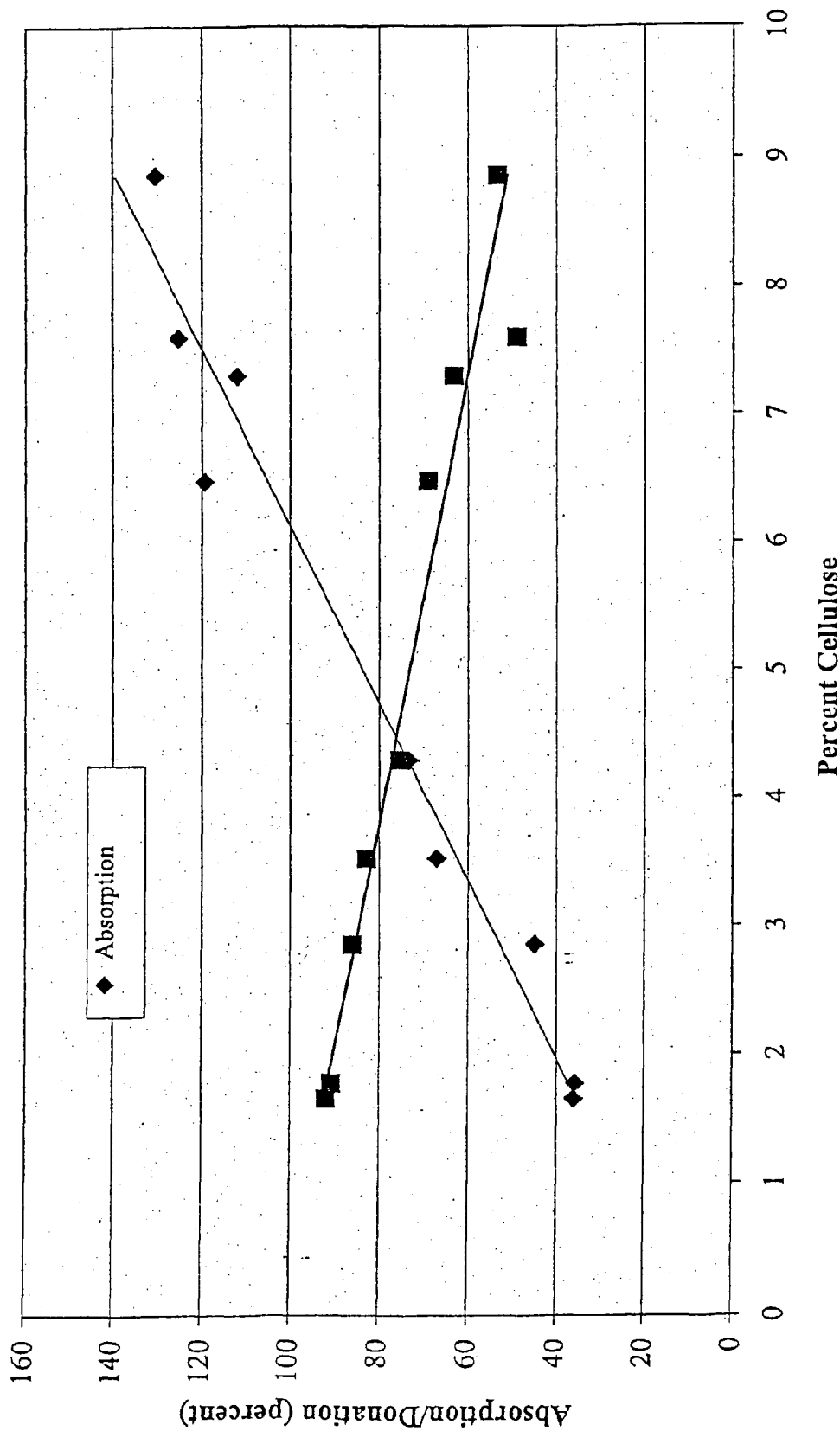

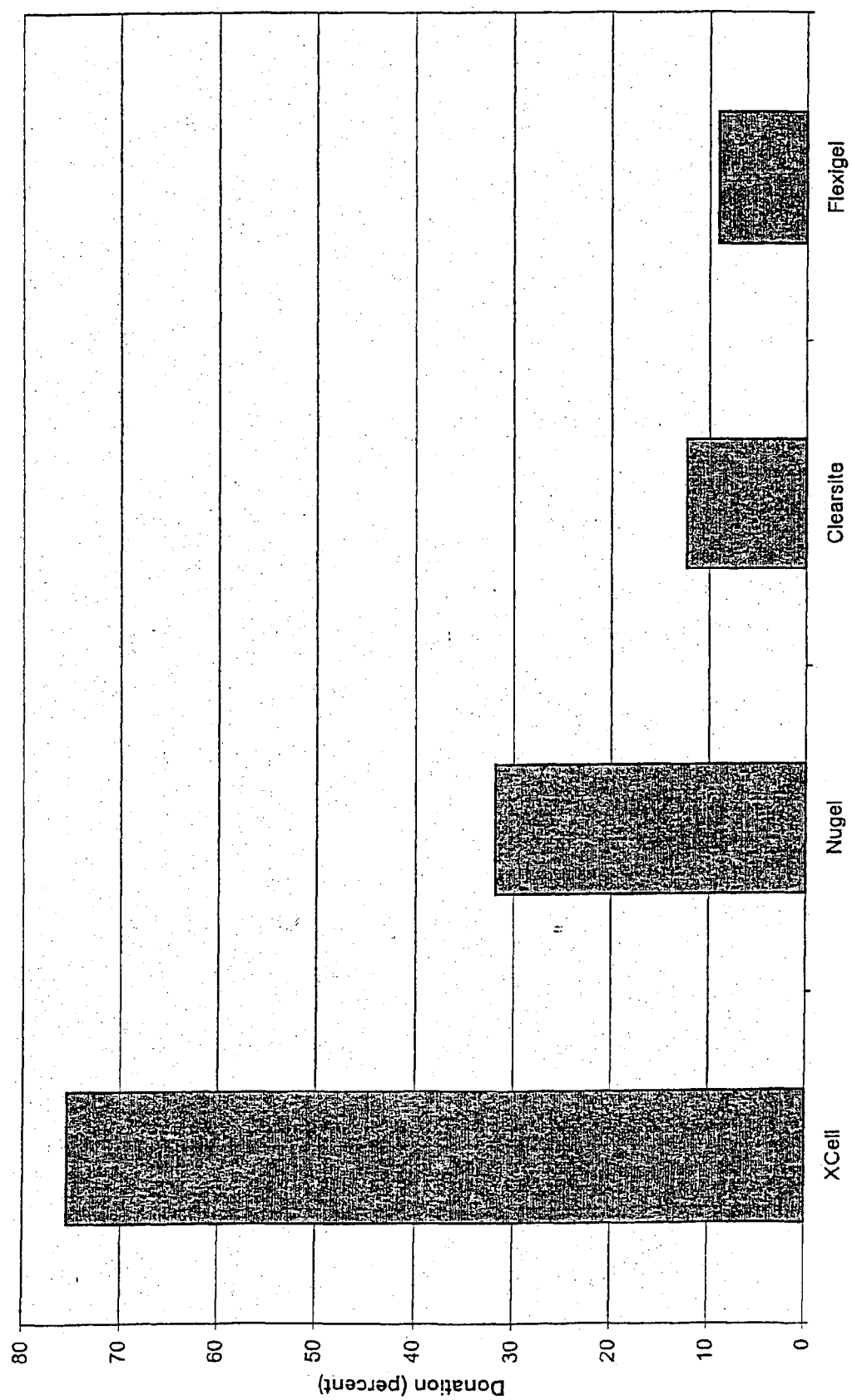

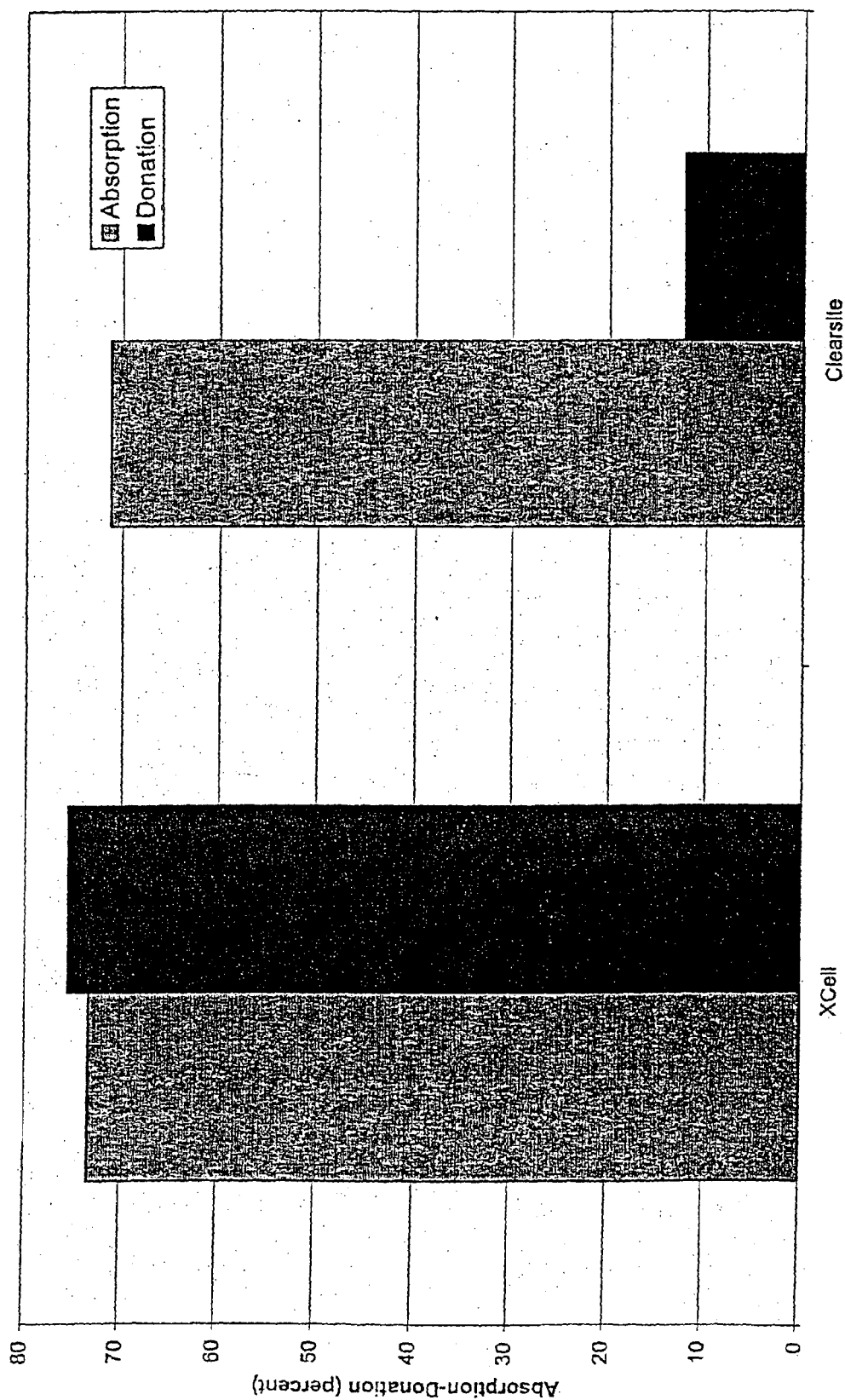

MICROBIAL CELLULOSE WOUND DRESSING FOR TREATING CHRONIC WOUNDS

CROSS REFERENCE TO RELATED APPLICATION

This is a Continuation-in-Part of application Ser. No. 10/132,171, filed Apr. 26, 2002. The disclosure of this application is incorporated herein by reference.

FIELD OF THE INVENTION

The invention relates to a wound dressing comprising a microbial-derived cellulose for treatment of specific types of chronic wounds, including pressure sores, venous and diabetic ulcers. This invention also relates to a microbial-derived cellulose wound dressing containing antimicrobial additives that provide the capability to inhibit the growth of microorganisms on the dressing surface in contact with a wound. The antimicrobial wound dressing may contain compounds such as polyhexamethylene biguanide(PHMB).

BACKGROUND OF THE INVENTION

There are a wide variety of materials used to fabricate wound dressings, which are used to treat a host of surgical and non-surgical lesions, such as burns and abrasions. The dressings range from simple gauze-type dressings to animal derived protein-type dressings such as collagen dressings, the composition of the particular dressing depends on the type of wound to be treated. Each of these dressings has advantages depending upon the type of application. For example, gauze-type dressings are sufficient and highly economical for simple abrasions and surgical incisions.

On the other hand, in cases of chronic wounds, polymer-based dressings are found to be more effective. By definition, chronic wounds are wounds that fail to proceed through the normal repair process and are typically manifestations of an underlying problem such as diabetes, venous disease or impaired circulation (Lazarus, G.S. et al., *Definitions and Guidelines for Assessment of Wounds and Evaluation of Healing*, Arch. Dermatology, vol. 130, pages 489-493, 1994). Thus, chronic wounds can be broadly categorized as pressure sores (decubitus), venous and diabetic ulcers depending on the underlying problem. Depending on the cause, various types of wound management treatments and materials are used to address the underlying problem and promote wound healing. Advanced polymeric materials with the capability of maintaining moist wound environment have been shown to be more effective than gauze in treating these difficult to heal chronic wounds.

Within the context of polymer-based dressings, various types of polymeric materials have been used in the treatment of skin disorders. Generally, they can be broken down into two major classes, namely synthetic and naturally derived polymeric materials.

Synthetic materials include polyurethanes, polyvinylpyrolidone (PVP), polyethyleneoxide (PEO), polyvinyl alcohol (PVA), and polyacrylonitrile (PAN). These materials may be used in combination with other synthetic or natural polymers to fabricate wound dressings with specific properties such as moisture retention and high fluid absorption. Both of these properties, generally not found in gauze-type dressings, promote healing by protecting chronic wounds from infection and maintaining moisture levels in the wound. Huang discloses in U.S. Pat. No. 6,238,691 a three dimensional crosslinked polyurethane hydrogel wound dressing, which is absorptive, contours to a wound site and maintains the wound in a moist state to promote healing.

Meyer-Ingold et. al. disclose in U.S. Pat. No. 6,156,334, wound coverings for the removal of interfering factors, such as antigens, free radicals, ions, proteins, peptides, lipids and free fatty acids, in the wound fluid of chronic wounds. These wound coverings are chemically modified with "trapper molecules", such as antibodies, chelators, enzyme inhibitors, enzymes, enzyme mimics, peptides and other proteins, are polyurethane or plant-derived cellulose.

Similarly, naturally derived polymers or biopolymers, such as collagen and alginates, have also been used as wound dressings that exploit the desirable characteristics of the polymers, such as high absorption capacity of alginate or the biocompatible nature of collagen. Each of these dressings has associated particular advantages depending on the type of wound and amount of exudate it generates. However, these dressings also have disadvantages, which include higher cost, wound adherence, limited exudate absorption and residue deposition on a wound site.

Hydrocolloid dressings absorb wound exudate and provide a moist wound-healing environment, but also have the undesirable characteristic of residue deposition on a wound site. Additionally, unlike the microbial-derived cellulose dressing described herein, hydrocolloid dressings lack a moisture-donating feature necessary for dry chronic wounds with limited exudate. Also, hydrocolloids are known to adhere to the wound bed and can cause reinjury upon removal. Hydrocolloids have a tendency to break down in the wound bed possibly interfering with the wound healing process.

As an alternate material, microbial-derived cellulose possesses inherent characteristics which allow for effective promotion of wound healing without some of the inherent disadvantages associated with current wound dressings. In this regard, microbial-derived cellulose possesses the following physical properties that distinguish it from plant-derived cellulose such as extreme hydrophilicity and unique multi-layered three dimensional laminar structures that provide its moisture handling ability. Microbial cellulose is highly hydrophilic with a water-holding capacity ranging from 60 to 700 times its own weight as is described in U.S. Pat. No. 4,942,128. Microbial cellulose also demonstrates excellent wet strength and does not breakdown under compression. Lastly, because of its laminar multi-layered structure, microbial cellulose can be processed to produce a film with novel fluid handling ability. By adjusting the cellulose to liquid ratio, processed microbial cellulose is capable of both donating fluid or absorbing liquid depending on the surface the film is made to come in contact with.

Because of its superior characteristics, use of microbial cellulose in the medical industry has been previously investigated. For example, U.S. Pat. Nos. 4,588,400, 4,655,758 and 4,788,146 to Ring et al. disclose the possible use of microbial-derived cellulose in liquid-loaded medical pads. The patents to Ring et al focus on using statically produced microbial cellulose pads loaded with various liquids and medicaments. Various types of liquids that can be contained in the microbial cellulose pad were detailed as well as the production and cleaning method to produce the starting cellulose material. Also described in these patents are examples which detailed methods of fabrication of various pads wherein the method involves a series of pressing and soaking steps to adjust the physical properties, mainly with respect to the liquid to cellulose ratio to yield a desired product. As an example, these patents illustrate a highly hydrated pad (80 to 1 fluid to cellulose ratio) which is able to provide a cooling capability which is ideal for burn applications. In particular, the '146 patent describes the use of such liquid loaded pads as wet dressings for use as an ulcer dressing capable of providing moisture to the wound over an extended period of time. The same '146 patent also mentions that the wet dressings described in the examples also have the additional ability to absorb large quantities of fluid from the wound site when the dressing is applied in a less than saturated condition. However, the wound dressings of Ring et al. fail to mention a singular dressing having both the ability to be a source of moisture for chronic wounds as well as the ability to absorb fluid. The Ring et al. patents also fail to describe the effective liquid to cellulose ratio to fabricate a dressing having the dual fluid handing capability and also fail to disclose any particular benefits from the combination of microbial cellulose and an antimicrobial agent.

In particular, Ring fails to disclose levels of antimicrobial agents which would be non-irritating, non-cytotoxic and non-sensitizing. Additionally, Ring does not disclose which agents would be stable to gamma sterilization.

U.S. Pat. No. 4,912,049 to Farah et al. discloses the use of statically produced dehydrated microbial cellulose as an artificial skin graft, a separating membrane or artificial leather. The '049 patent recites the use of a cellulose film formed by Acetobacter xylinum that is dehydrated while it is stretched. Although the '049 patent described potential use of their invention as an artificial skin for treatment of wounds or injury, there is no suggestion that the material could be used for chronic wounds. Furthermore, the dried film of Farah has no moisture donation capability and minimal absorption capacity. Farah fails to disclose any particular benefit from the combination of microbial cellulose and an antimicrobial agent.

Finally, U.S. Pat. No. 5,846,213 by Wan et al. discloses methods of preparing microbial cellulose films using raw material produced in a stirred-tank bioreactor, instead of the static method. The '213 patent further describes the use of such cellulose material dissolved in solvents to fabricate membranes that can be use as wound dressings. Because of its dry nature of the resulting film, the cast material lacks any moisture donating ability and limited fluid absorption capacity. Also, the resulting cellulose membrane does not possess the three dimensional multi-layered structure found only in statically grown microbial cellulose as previously described. As with Ring et. al. and Farah, no disclosure of any particular benefit from the combination of microbial cellulose and an antimicrobial is made by Wan.

The use of additives in wound dressings to impart antimicrobial or inhibitory activity has been investigated. Silver based compounds (Arglaes and Acticoat dressings), chlorhexidine gluconate (Chlorhexidine Gauze Dressing BP), benzalkonium chloride (Band-Aid brand gauze dressing), parabens (NugelDressing), and PHMB (Kerlix and Excilon gauze dressings) have been incorporated into commercially available wound dressings in order to impart an antimicrobial or bioinhibitory property to the dressing. Ring in the '400 patent indicated in his claims the use of additives on liquid loaded medical pads made from microbial-derived cellulose, but failed to disclose any particular benefits from the combination of microbial cellulose and an antimicrobial agent. In particular, Ring fails to disclose levels of antimicrobial agents which would be non-irritating, non-cytotoxic and non-sensitizing. Additionally, Ring does not disclose which agents would be stable to gamma sterilization.

PHMB is a cosmetic preservative provided as a 20% solution in water under the trade name Cosmocil CQ. The use concentration in cosmetics is 0.2-1.0% of the 20% solution. The 20% concentrate is a strong irritant. Fifty thousand ppm was tolerated by rats, with no irritation. No sensitization was observed, in a guinea pig sensitization test. (Cosmetic and Drug Preservation: Principles and Practice, Ed. Jon J. Kabara. Marcel Dekker, Inc. New York and Basel. pp 728-730. 1984).

Brown described in U.S. Pat. No. 4,643,181 a surgical dressing or drape material coated with a solvent based contact adhesive, which contains polyhexamethylene biguanide hydrochloride dispersed therein.

Orr disclosed in U.S. Pat. No. 6,369,289 a cellulosic bandage consisting essentially of an antimicrobial amount of polyhexamethylene biguanide hydrochloride applied to the bandage, a method of covering an open wound with said bandage, and a method for the preparation of the same. The dressing described in Orr's '289 patent does not have the moisture donating capability demonstrated by the microbial-derived cellulose of the present invention.

In U.S. Pat. No. 4,655,756 Fawkes disclosed a non-woven material treated with a linear polymeric biguanide, preferably polyhexamethylene biguanide hydrochloride. The treated non-woven material is used to construct disposable nappies, which have reduced odor due to the antimicrobial activity of polyhexamethylene biguanide hydrochloride.

Quantrille in U.S. Pat. No. 4,837,079 discloses a non-woven web used as wet wipe containing polyhexamethylene biguanide hydrochloride, and a method for the preparation of the antimicrobial containing non-woven web. Unlike Fawkes, this invention produces a non-woven in which the polyhexamethylene biguanide hydrochloride is substantive to the web and binder. This substantive characteristic improves antimicrobial activity at lower concentrations and reduces irritation to users of the material.

Although the above patents recognize the potential use of microbial cellulose in medical applications, the prior art has failed to provide a method of developing a wound dressing which demonstrates effective wound healing, moisture management capability, antimicrobial activity, and adequate biocompatibility. Accordingly, an effective wound dressing comprising microbial cellulose for treatment of chronic wounds, which is highly biocompatible, is desirable. Furthermore, a wound dressing with high moisture donation and absorption capabilities is also particularly desirable for optimal wound healing. This dual moisture handling ability of the dressing of the present invention is capable of maintaining a moist wound environment necessary for healing chronic wounds. Also, the high moisture donation ability is particularly useful for treating dry necrotic tissue and promoting autolytic debridement that is desirable for any wound closure to be possible. Additionally, the ability of the wound dressing of the present invention in assisting autologous healing by promoting granulation and allowing epithelial cells to migrate exhibits the distinct ability of the wound dressing in effecting wound closure. Finally, the incorporation of an antimicrobial agent into the wound dressing will further enhance the healing process by combating or preventing microbial infections.

Thus, the present inventors have developed a wound dressing which possesses this novel fluid handling capability of absorption and donation. This fluid handling capability is an end result of the processing microbial cellulose to contain the proper cellulose content for the intended purpose. The resulting wound dressing can donate fluid if the wound surface is dry and found to be particularly useful for dry chronic wounds covered with dry necrotic tissue or eschar. The same dressing is also capable of absorbing fluid away from the exuding wound bed. Additionally, the microbial cellulose wound dressing described in this invention will not degrade and leave a residue in the wound site, unlike hydrocolloid dressings. Removal of the microbial cellulose dressing from the wound does not damage tissue because it does not adhere to the wound surface.

The present invention also envisages microbial cellulose sheets which can be directly synthesized in virtually any shape or size. Fermentation processes yield an extremely thin and pliable form, which is remarkably strong, yet, gas and liquid permeable. The shape will remain intact even when subjected to extreme environmental conditions such as autoclaving or gamma sterilization.

SUMMARY OF THE INVENTION

It is an object of the present invention to provide methods for treating chronic wounds with a microbial-derived cellulose dressings 1.5 to 9% cellulose by weight. In a preferred embodiment, the microbial-derived cellulose is biocompatible and nonpyrogenic.

It is another object of the present invention to provide an effective wound dressing comprising microbial cellulose for treatment of chronic wounds that is capable of donating and absorbing moisture for optimal wound healing.

It is a further object of the present invention to provide antimicrobial or bioinhibitory activity to the wound dressing by incorporation of suitable agents, specifically polyhexamethylene biguande hydrochloride, into microbial-derived cellulose for the treatment of infected chronic wounds or prevention of infection in chronic wounds. The most preferred range of PHMB in the microbial- derived cellulose wound dressing is 2700-3700 ppm. (See Tables 1 and 2).

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

FIG. 1: The absorption and donation capabilities of microbial cellulose wound dressings are shown versus the percent cellulose contained in the materials. All materials were of identical area and similar thickness. The region of intersection of the two curves shows the ideal cellulose content to maximize both properties.

FIG. 2: The amount of fluid donated to a dry surface from XCell microbial cellulose wound dressing and from hydrogel wound dressings is shown. Donation quantities are expressed as a percent of the original sample weight. The donation of the XCell wound dressing is markedly superior to that of the hydrogels.

FIG. 3: The absorption and donation capabilities of XCell microbial cellulose wound dressing are compared to that of Clearsite (NDM) hydrogel wound dressing. The absorptive capacity is nearly identical for the two, but the XCell wound dressing can donate 6 times more than the hydrogel.

DETAILED DESCRIPTION OF THE PREFERRED EMBODIMENT

The invention provides methods for treating full or partial thickness chronic wounds with microbial-derived cellulose. The invention also provides biocompatible, nonpyrogenic microbial-derived wound dressings with a proper cellulose to liquid ratio as well as, liquid donation and absorption capability for optimal wound healing. Unlike hydrocolloid, hydrogel, alginate, collagen, or gauze dressings the microbial-derived cellulose dressing described herein, can provide an optimal moist healing environment by donating fluid to dry surface or absorbing excess fluid from exudating wounds.

The content of microbial-derived cellulose present in the dressing can fluctuate depending upon the method of preparation and the eventual end use of the wound dressing. In the present invention, the amount of microbial-derived cellulose present in the wound dressing is about 1.5% to about 9%, preferably it is about 3% to about 7%, more preferably about 4% to about 6% by weight. The most preferred range of PHMB in the microbial- derived cellulose wound dressing is 2700-3700 ppm. (See Tables 1 and 2).

The wound dressing of the present invention can be used for moisture donation. This means that a wound which exhibits dry necrotic tissue can be effectively treated by application of a fluid containing wound dressing. Most chronic wounds when they initially surface usually form a dry surface composed of dead (necrotic) tissue due to an underlying problem such venous insufficiency. The lack of fresh blood flow to the particular area (usually around the ankle) causes the dermis and epidermis to die underneath the skin and eventually surfacing as an ulcer. Liquid contained in the wound dressing pad can be applied to the dry, necrotic wound to promote autolytic debridement which is the first requirement of healing chronic wounds. Liquid materials which can be loaded into the pad include but are not limited to water, saline, glycerin, synthetic polymers such as polyethylene oxide and solutions of biological molecules including proteins and enzyme such as collagenase.

The wound dressing of the present invention also can be used for moisture absorption. This means that a wound which is exudating can be effectively treated by application of a wound dressing of the present invention which will absorb excess fluid from the wound. Typically, chronic wounds such venous ulcers tend to exude large amount fluids during the healing process. The exudation stage usually occurs when the wound begins to form granulation tissue to fill up the space the dead dermal tissue use to occupy. At this stage the dressing of the present invention is able to absorb the fluid exudate while keeping a moist surface for epithelial cells to migrate. The epithelial migration is essential for eventually closing the wound. Thus, the wound dressing of this invention is able to provide optimum conditions for wound healing due to its dual ability to absorb and donate moisture.

1. Production of Microbial Cellulose Under Static Conditions for Testing Procedures In preparing the microbial cellulose of the invention, microorganisms such as Acetobacter xylinum are cultured in a bioreactor containing a liquid nutrient medium at 30 degrees ° C. at an initial pH of 3-6. The medium is based on sucrose or other carbohydrates. Preferably, efficient film production is achieved using sucrose as a carbon source, ammonium salts as a nitrogen source, and corn steep liquor as nutrient source coupled with a proprietary trace elements supplement, which varies from the original Schramm & Hestrin medium (1954) used by those skilled in the art. This proprietary trace elements supplement is quantified in the following table:

TABLE 1

| Trace Element Solution | (Composition per Liter) |
|---|---|
| EDTA Tetrasodium Salt | 570 mg |
| $FeSO_4 \cdot 7H_2O$ | 200 mg |
| $ZnSO_4 \cdot 7H_2O$ | 10 mg |
| $MnSO_4 \cdot H_2O$ | 26 mg |
| $H_3BO_3$ | 30 mg |
| $CoCl_3 \cdot 6H_2O$ | 20 mg |
| $NiCl_2 \cdot 6H_2O$ | 3.2 mg |
| $(NH_4)_6Mo_7O_{14} \cdot 4H_2O$ | 2.4 mg |

Two ml of this solution is added per liter of media.

Suitable bioreactors are selected which minimize evaporation and provide adequate oxygen-limiting conditions. Oxygen-limiting conditions may be varied depending upon the desired water content and thickness of the cellulose film. Generally, under oxygen-limited conditions, oxygen is present in an amount of 5%-21% of the total gas present at the air liquid interface. The bioreactor is composed of plastic box fitted with an airtight cover or a limited gas-permeable cover. Dimensions of the bioreactor can vary in configuration (cube or cylinder) depending on the shape and size of the cellulose film being produced. For example, a six inch diameter cylinder will produce a six inch diameter dressing, which can be used as is or cut to conform to the wound to be treated, prior to application. By limiting the amount of oxygen in the fermentation medium, it is hypothesized that the Acetobacter utilizes the carbon available in the medium to produce more cellulose instead of using it for reproduction, thereby increasing the total yield of cellulose.

The fermentation process under static conditions was allowed to progress over for a period of about 7-30 days, during which the bacteria in the culture medium produced an intact cellulose pellicle containing the microorganisms. Depending on the desired thickness, which corresponds to a certain cellulose content per unit area, the fermentation is stopped and the pellicle is removed from the bioreactor. The excess medium contained in the pellicle is then removed by standard separation techniques such as compression or centrifugation prior to chemical cleaning and subsequent processing of the pellicle to yield a wound dressing with a cellulose to liquid ratio of about 1:10 to about 1:65. The raw cellulose pellicle has an increased sugar:cellulose yield of about 35%, compared to literature values of 10%. This increased yield coupled with an inexpensive nitrogen source resulted in a 40-fold reduction in production-cost of the raw cellulose film as compared to cellulose films produced according to the original Schramm & Hestrin medium [1954, J. Gen. Micro, 11:123-129].

2. Processing and Depyrogenation Procedures

After the cellulose film has been produced, the cells have to be removed from the cellulose pellicle for purification. Fontana et al. (1990, Appl. Biochem. Biotech, 24: 253-264) have described the cells as being apyrogenic, however, the unpurified cellulose pellicle has tested positive for pyrogens using the Limulus Amebocyte Lysate (LAL) test kit. This result necessitated the removal of the cells by chemical processing discussed here in order to pass the standard pyrogenicity test and qualify the microbial cellulose wound dressing as non-pyrogenic.

The cellulose pellicle is subjected to a series of chemical wash steps to convert the raw cellulose film into a medical grade and non-pyrogenic wound dressing material. Typical processing uses hydroxide solutions at concentrations of 1-20% by weight. Preferably, sodium hydroxide is used at a concentration of not less than 3% and most preferably about 3% to about 5% in order to acetylate and eventually dissolve the cells. In addition, the present invention provides hydrogen peroxide washing capable of bleaching and sterilizing the pyrogen free films. Concentrations of about 0.05% to about 10% peroxide by weight are useful to effect whitening of the films. Preferably the amount of peroxide used in about 0.1% to about 0.5%.

Purification processes using various exposure times, concentrations and temperatures were conducted on the raw fermentation product. Processing times of 1-4 hours have been studied in conjunction with temperature variations of 30-100 degrees centigrade to optimize the process. The resulting films from each of the different operating conditions were tested for their respective pyrogen levels and physical characteristics. The process condition that yields a nonpyrogenic product in the least amount of time and lowest chemical concentration was then selected for economic reasons. The time involved in this process can be as much as 4 hours at about 90° C., preferably the time involved is about 1-2 hours at about 60° to about 80° C.

The amount of cellular debris left in the cellulose pad after processing may be measured by Limulus Ameabocyte Lysate (LAL) test as outlined by the U.S. Food and Drug Administration (FDA) in 21 CFR10.90. The instant cleaning process outlined above provided a nonpyrogenic cellulose pad (<0.05 EU/ml). The allowable pyrogen content in Class I medical devices is 0.5 EU/ml (FDA LAL test Guideline). The steps of the LAL test are defined by the test kit manufacturer and can simply be followed to yield the pyrogen level in the cellulose film.

3. Physical Modification of Microbial Cellulose Dressing

Desirable characteristics of a wound dressing material include an ability to provide a moist environment, and yet at the same time, the ability to absorb excess exudate fluid from, or donate moisture to, a wound. Currently marketed hydrogel wound dressing products have an approximate composition of 90-95% water and 5-10% polymer material. However, these products fail to provide adequate moisture to the wound and are characterized by inadequate strength. Furthermore, these dressing tend to adhere to the wound site. This wound adhesion results in reinjury of the wound upon removal. The dressings of the instant invention however display superior moistness and absorptivity due to a laminar multi-layered three-dimensional structure not found in any other wound dressing. The cellulose dressing has also displayed the ability to control the level of moisture in the dressing wound interface by absorbing excess fluid or donating moisture depending on the conditions at the wound site. This moisture management capability helps in the promotion of healing in chronic wounds and is a novel characteristic of the cellulose wound dressing.

Cellulose pellicles typically have an initial composition of >90% water and 0.2-1% cellulose or a cellulose to water ratio of approximately 1:100-1:500. This material is subjected to series of physical treatments to derive the final wound dressing. Water content of a saturated microbial cellulose pad may be reduced to between 98%-0% giving films with cellulose to water ratio of approximately 1:50 to 1:0, i.e., completely dry material. This may be accomplished using different drying techniques, including mechanical pressing, centrifugal draining, air drying, vacuum drying and freeze drying. After mechanical pressing to a desired cellulose to water ratio, the dressings are soaked in a 5000ppm aqueous solution of PHMB for 4+/−0.25 hours with no agitation. The dressing is then compressed to extract several ml of solution. The resultant solution is diluted and assayed for PHMB with a UV/VIS spectrophotometer at 234 nm.

The resulting dehydrated pads were then tested for their absorption capability by completely immersing them in water. The results show that the completely dried material had a reduced ability to reabsorb water as compared to the never-dried material. The completely dehydrated pads absorbed in 24 hours only a maximum of 30 grams water per 100 cm$^2$ pad, while the nondehydrated pads absorbed as much as 60 grams/100 cm$^2$ over the same period. In this regard, wound dressings of the instant invention contain a cellulose to water ratio of about 1:40 to 1:5 and preferably about 1:30 to about 1:10. These wound dressings display the ability to provide a moist environment and yet have the dual ability to donate moisture or absorb exudate fluid for optimal wound healing.

4. Product Packaging and Sterilization

Packaging material should be impermeable to water to prevent the moist cellulose wound dressing from drying out, and be able to withstand the sterilization process. For example, an aluminum plastic-coated heat-sealable chevron pouch provides adequate impermeability and moisture retention.

The two most commonly used sterilization procedures for medical wound dressings, gamma irradiation and electron beam sterilization, were both investigated. The packaged cellulose wound dressings were exposed at different levels of radiation ranging from 5-50 KGray. The sterility of each dressing was then evaluated using standard USP sterility tests. The overall appearance and mechanical integrity of the dressing and the packaging material was also examined. The results of the sterility testing showed that the cellulose wound dressing was stable at the 5-40 KGray radiation dose and a minimum dose of 15 KGray was required to assure product sterility. Cellulose wound dressing products that were to be used for the biocompatibility, animal and human tests were then all sterilized at 30 KGray (two-fold safety factor) to assure product sterility. Unlike chlorhexidine gluconate and neomycin sulfate, PHMB is stable when exposed to gamma radiation at doses used to sterilize the dressing.

BIOLOGICAL EXAMPLES

Example 1

Absorption/Donation Studies

Cellulose pellicles of varying thickness were produced and processed to remove cellular debris. Pellicles were compressed to a uniform thickness of 1.9 mm, yielding a series of films with cellulose contents ranging from 1.5% to 10%. These films were tested for the ability to absorb saline from a saturated surface, and to donate moisture to a dry surface.

Weighed samples of uniform area were placed on the surface of a saturated sponge. Saline was poured around the sponge to maintain saturation. After 24 hr, the samples were reweighed to determine absorption, which was then plotted as percent of initial sample weight. To determine the moisture donation, weighed samples of uniform area were placed on the surface of smooth, dry leather. The leather was weighed prior to addition of sample. After 2 hr, the sample was removed and the leather was reweighed to determine the quantity of moisture that was donated, which again was plotted as percent of the initial sample weight.

Both absorption and donation data were plotted on one graph to determine the optimal water content for both properties. This data is shown in FIG. 1. From this figure it can be seen that in order to possess absorption and donation capabilities, the cellulose percentage in the dressing should ideally be in the range of 3% to 6%. The figure also shows that one could make a dressing that would have either enhanced absorption or enhanced donation, at the expense of the other property.

In order to show the superiority of the donation capability of the microbial cellulose wound dressing (Xcell), tests were performed on traditional hydrogels in the market. Products tested were Clearsite (NDM), Nugel (Johnson&Johnson) and Flexigel (Smith&Nephew). The same procedure described above was performed for these products, with data shown in FIG. 2. The XCell data used was for material containing 4.3% cellulose. As is clearly evident, the XCell dressing donated over 75% of its initial weight, outperforming all competitor products, which donated between 9% and 31%.

Although donation is very important for wound healing, a wound dressing would be ideal if it had the ability to donate and absorb. The procedure described previously for absorption was used to test Clearsite hydrogel wound dressing. The data for this is shown in FIG. 3, along with donation data and XCell data. As can be seen, the absorption of both samples is nearly identical, but the XCell material donated six times more moisture than the hydrogel.

Samples of Xcell containing 2700 ppm PHMB were evaluated for their moisture donation and absorption ability. Average moisture absorption with 2700 ppm PHMB is 75.6% vs 71.5% without PHMB: average moisture donation is 80.7% with 2700 ppm PHMB vs 79.0% without PHMB. Neither moisture donation or absorption is significantly changed by the addition of 2700 ppm PHMB.

Example 2

Biocompatibility Testing

The sterile cellulose wound dressing was subjected to the following biocompatibility tests: 1) Guinea pig sensitization, 2) Primary irritation in rabbits and, 3) Cellular cytotoxicity. In the sensitization test, extracts of the product were injected into six guinea pigs. The body temperatures of the guinea pigs were monitored for any sensitization reaction during the 8-10 week study period. The results showed no evidence of delayed dermal contact sensitization in the guinea pigs. The Primary irritation test was a two-week study using rabbits. In this test, extracts of the cellulose dressing were injected subcutaneously and the skin was observed for any irritation reactions. The results showed that there was no evidence of significant irritation or toxicity from the subcutaneous injection of the extract into rabbits. The Primary Irritation Index of the cellulose dressing extract was found to be negligible. Finally, the cytotoxity of the dressing with mammalian cells was tested using murine L929 cell culture. The results indicated that an extract of the cellulose dressing was not cytotoxic and did not inhibit cell growth. The cellulose wound dressing prepared by the instant invention successfully passed all of these tests thus assuring that the product is biocompatible, safe and will not inhibit wound healing.

Additionally, various levels of PHMB were tested for cytotoxicity, sensitization, irritation, hemolysis and acute systemic toxicity using procedures described in Table 1. Results are summarized in Table 1.

PHMB is not cytotoxic as determined by an ISO Agarose Overlay Method (solid) up to 3700 ppm. PHMB is not a sensitizer as determined by an ISO Maximization Sensitization Study (extract) method up to 15700 ppm. PHMB is not an irritant as determined by an ISO Intracutaneous Study (Extract) up to 7900 ppm. PHMB is not hemolytic or demonstrate systemic toxicity at 2700 ppm. Unlike the cellulose gauze dressing described in Orr's '289 patent, the data in Table 2 suggest that PHMB may be used without irritation in a microbial-derived cellulose dressing at levels which significantly exceed the 500-3000 ppm non-irritating PHMB range suggested by Orr in his '289 patent.

TABLE 2

| Cosmocil | PHMB Concentration (ppm) | | | | | | |
|---|---|---|---|---|---|---|---|
| | 540 | 1700 | 2700 | 3700 | 7900 | 12200 | 15700 |
| Cytotoxicity (Agarose Overlay) | None | None | None | None | Yes | Yes | |
| Sensitization | | | | | None | | None |
| Irritation | | | | | None | | Yes |
| Hemolysis | | | None | | | | |
| Acute Systemic Toxicity | | | None | | | | |

| Test | Method |
|---|---|
| Cytotoxicity | ISO Agarose Overlay Method (solid) |
| Sensitization | ISO Maximization Sensitization Study (extract) |
| Irritation | ISO Intracutaneous Study (Extract) |
| Hemolysis | In vitro Hemolysis Study (Modified ASTM Extraction) |
| Acute Systemic Toxicity | USP and ISO Systemic Toxicity Study (Saline and Cottonseed) |

Example 3

Wound Healing in Animal Models

The objective of animal pre-clinical studies was to compare the wound healing performance in animal porcine models of the microbial derived cellulose wound dressing with existing wound dressing products such as hydrocolloids and hydrogels.

The test was conducted using the porcine model protocol of the Department of Dermatology of the University of Miami School of Medicine in compliance with Association for Accreditation of Laboratory Animal Care (AAALAC).

Briefly, the test was conducted on 2 pathogen-free pigs over a seven-day period. Approximately 140 rectangular wounds (10×7×0.3 mm) were made in the paravertebral and thoracic area of each pig with a specialized electrokeratome fitted with a 7 mm blade. The wounds are separated from one another by a 15 mm of unwounded skin. About 35 wounds were randomly assigned to each wound dressing treatment group of cellulose, hydrocolloid, hydrogel and no dressing/air exposed. An epidermal migration assessment was started two days after application.

In summary, the results showed that the cellulose wound dressing healed the partial thickness wounds as well as the hydrocolloid dressing and better than the hydrogel dressing. Significantly, on the fourth day after wounding, the cellulose wound dressing healed 70% of the wounds as compared to 50%, 20% and 0% for the hydrocolloid, hydrogel and air-exposed wounds, respectively. By the fifth day, both cellulose and hydrocolloid dressings had both healed 100% of the sampled wounds, while the hydrogel and air exposed samples were only 70% and 50% healed, respectively.

Example 4

Human Clinical Effectiveness Testing in Treating Chronic Wounds

The objective of the human clinical testing was to assess the effectiveness of the cellulose wound dressing in treating various types of chronic wounds. A total of 29 patients with 31 various types of chronic wounds were involved in the study. The patients were treated with the cellulose wound dressing after passing the inclusion criteria outlined in the study protocol approved by an institutional review board (IRB). The cellulose wound dressing treatment was implemented for eight weeks or until the wound healed. Weekly wound observations were conducted. After the observations were recorded the dressings were changed. Both wound condition and size were recorded during the weekly visits and the study was terminated after the wounds healed or eight weeks of treatment.

The results of the human study can be divided into three notable indications based on the performance of the cellulose wound dressing. The cellulose wound dressing exhibited strength in the removal of slough necrosis in deep pressure ulcers. Application of the cellulose wound dressing reduced the hypergranulation tissue down to the level of the surrounding epithelium in two wound presented with the problem. The third and most interesting response to the cellulose wound dressing was observed during the treatment of venous leg ulcers, particularly those with full thickness tissue involvement. The results showed that out of thirteen (13) venous leg ulcers (two partial thickness and eleven full thickness wounds), seven (54%) were completely healed and the remainder (46%) showed improvement during the course of the eight-week study.

Example 5

Antimicrobial Testing

The antimicrobial efficacy of PHMB at 2700 ppm was demonstrated against a variety of microorganisms using three separate methods. The data is summarized in Table 3. At 2700 ppm PHMB inhibits the growth of 14 microbes/strains as demonstrated by a Microbial Barrier/ Strike-through Test. At 2700 ppm PHMB kills 99.2-99.9% of 5 microorganisms as demonstrated by AATCC Test Method 100, modified. Also, no growth of *Aspergillus niger* is observed on a dressing sample containing 2700 ppm PHMB as demonstrated by AATCC Test Method 30-Part III. Kerlix and Excilon are gauze dressings containing 2000 ppm PHMB. In a comparison of these gauze dressings with XCell dressing with 2700 ppm PHMB (Table 3), the gauze dressings show macroscopic growth of *Aspergillus niger* and no reduction of *Pseudomonas aeruginosa* (Kerlix) or *Staphylococcus aureus* (Excilon), while the XCell dressing exhibits no growth of *Aspergillus niger* and >99.2% reduction of all organisms tested. The unique characteristics of XCell allow for the use of higher concentrations of PHMB, assuring superior reduction or inhibition of microbial growth, without cytotoxicity which may inhibit healing (Table 2).

TABLE 3

Microbial Barrier/Strike-through Test (PHMB at 2700 ppm)

| Organism | ATCC #/ Resistance | Result |
|---|---|---|
| *Aspergillus niger* | 16404 | No Growth |
| *Candida albicans* | 10231 | No Growth |
| *Enterobacter cloacae* | 13047 | No Growth |
| *Enterococcus faecalis* | 51575/ VRE | No Growth |
| *Escherichia coli* | 8739 | No Growth |
| *Klebsiella pneumoniae* | 4352 | No Growth |

TABLE 3-continued

| | | |
|---|---|---|
| Proteus mirabilis | 25933 | No Growth |
| Proteus vulgaris | 33420 | No Growth |
| Serratia marcescens | 13880 | No Growth |
| Staphylococcus aureus | 6538 | No Growth |
| Staphylococcus aureus | 33591/MRSA | No Growth |
| Staphylococcus epidermidis | 12228 | No Growth |
| Streptococcus pyogenes | 8668 | No Growth |
| Bacillus subtilis | 6051 | No Growth |

Assessment of antibacterial finishes on textile materials (AATCC Test Method 100, modified PHMB at 2700 ppm)

| Organism | ATCC # | % Reduction |
|---|---|---|
| Candida albicans | 10231 | 99.9 |
| Escherichia coli | 8739 | 99.9 |
| Staphylococcus aureus | 6538 | 99.5 |
| Pseudomonas aeruginosa | 9027 | 99.2 |
| Bacillus subtilis | 6051 | 99.9 |

AATCC Test Method 30-Part III (PHMB at 2700 ppm)

| Organism | ATCC # | Growth/Zone |
|---|---|---|
| Aspergillus niger Growth-on sample - Zone-around sample | 6275 | 0/no zone |

It will be apparent to those skilled in the art that various modifications and variations can be made in the methods and compositions of the present invention without departing from the spirit or scope of the invention. Thus, it is intended that the present invention cover the modifications and variations of this invention provided they come within the scope of the appended claims and their equivalents.

All publications, including patents and patent applications, mentioned herein above are hereby incorporated by reference to the same extent as if each was individually incorporated by reference.

What is claimed is:

1. A kit comprising:
(a) a nonpyrogenic microbial cellulose wound dressing consisting essentially of polyhexamethylene biguanide (PHMB), water and from 1.5 to 4.3 wt. % of microbial cellulose, said wound dressing made by a process that includes depyrogenating microbial cellulose pellicles to provide nonpyrogenic microbial cellulose wound dressing and adjusting the water content of the wound dressing to provide said wound dressing consisting essentially of water and from 1.5 to 4.3 wt. % microbial cellulose, wherein the wound dressing has not been completely dried;
(b) a moisture proof package containing said microbial cellulose wound dressing; and
(c) instructions for applying the microbial cellulose wound dressing to a chronic wound in a human patient; wherein the wound dressing absorbs fluid exudate in an amount that is about 20% to about 200% of its weight from an exuding chronic wound and donates moisture in an amount that is greater than 75% of its weight to a dry or necrotic portion of a chronic wound.

2. The kit of claim 1 which is sterilized by gamma irradiation.

3. The kit of claim 1 which is sterilized by electron beam sterilization.

4. The kit of claim 1, wherein the moisture-proof package containing the dressing comprises an aluminum plastic-coated heat sealable pouch.

5. The kit of claim 1 wherein the microbial cellulose wound dressing consists of water and 1.5 to 4.3 wt. % of microbial cellulose and PHMB.

6. The kit of claim 1 wherein said microbial cellulose wound dressing is shaped into the form of a wound.

7. The kit of claim 1 wherein said microbial cellulose wound dressing exhibits a negative Limulus Amebocyte Lysate test and is thereby nonpyrogenic.

8. The kit of claim 1 wherein said microbial cellulose wound dressing exhibits a negative primary irritation test in rabbits and a negative cytotoxicity test using murine L929 cells, passes a guinea pig sensitization test and is thereby biocompatible.

9. The kit of claim 1 wherein said microbial cellulose wound dressing is prepared. by a process that further includes the steps of: statically producing a microbial cellulose pellicles using Acetobacter xylinum; and isolating the pellicles with a cellulose to water ratio in the range of about 1:100 to about 1:500.

10. The kit of claim 9 wherein said microbial cellulose wound dressing is prepared according to the further step of purifying said microbial cellulose wound dressing by exposure to heat at 30 to 100° C. for about 1 to 4 hours.

11. The kit of claim 1, wherein said instructions comprise changing the wound from twice daily to weekly.

12. The kit of claim 1, wherein the microbial cellulose dressing has 2700-3700 ppm PHMB.

13. The kit of claim 1 wherein the microbial cellulose dressing is in a film form.

14. The kit of claim 13 wherein the microbial cellulose dressing wherein the film has a thickness of about 1.9 mm.

15. A method of treating a chronic wound with a would dressing as claimed in claim 1 comprising
applying the wound dressing of claim 1 to a chronic wound on a subject.

16. The method as claimed in claim 15 wherein said chronic wound is a full or partial thickness chronic wound.

17. The method as claimed in claim 15 wherein said chronic wound is a venous ulcer.

18. The method as claimed in claim 15, wherein said chronic wound is a pressure ulcer.

19. The method as claimed in claim 15, wherein said chronic wound is a diabetic ulcer.

* * * * *